United States Patent [19]

Steinman et al.

[11] Patent Number: 4,695,459
[45] Date of Patent: Sep. 22, 1987

[54] METHOD OF TREATING AUTOIMMUNE DISEASES THAT ARE MEDIATED BY LEU3/CD4 PHENOTYPE T CELLS

[75] Inventors: Lawrence Steinman; Matthew K. Waldor, both of Palo Alto, Calif.; Subramanian Sriram, Burlington, Vt.; Leonard A. Herzenberg; Leonore A. Herzenberg, both of Stanford, Calif.

[73] Assignee: The Board of Trustees of Leland Stanford Junior University, Stanford, Calif.

[21] Appl. No.: 686,126

[22] Filed: Dec. 26, 1984

[51] Int. Cl.$^4$ ............................................. A61K 35/56
[52] U.S. Cl. ...................................... 424/95; 514/825; 514/863; 514/866; 514/885
[58] Field of Search .................. 424/95; 514/825, 863, 514/866, 885

[56] References Cited

PUBLICATIONS

P. Y. Patterson in Autoimmunity, N. Talal, Ed. (Academic Press, NY, 1977), pp. 644–692.
B. G. Arnason, B. D. Jankovic, B. H. Waksman and C. Wennersten, J. Exp. Med., 116, 117 (1962).
N. K. Gonatas and J. C. Howard, Science, 186, 839 (1974).
L. Ortiz-Ortiz and W. O. Weigle, J. Exp. Med., 144, 604 (1976).
U. Traugott, E. L. Reinherz and C. S. Raine, Science, 219, 308 (1982).
C. B. Pettinelli and D. E. McFarlin, J. Immunol., 127, 1420 (1981).
Z. Lando and A. Ben-Nun, Clin. Immunol. & Immunopath., 290 (1984).
D. P. Dialynas et al, Immunol. Reviews, 74, 29 (1983).
E. L. Reinherz and S. F. Schlossman, N. Engl. J. Med., 303, 370 (1980).
E. L. Reinherz et al, N. Engl. J. Med., 303, 125 (1980).
P. Marrack et al, J. Exp. Med., 158, 1077 (1983).
S. P. Cobbold et al, Nature, 312 (1984).
S. W. Brostoff and D. W. Mason, J. Immunol., 133, 1938 (1984).
E. G. Engelman et al, Brief Definitive Report, 153 (1981), pp. 193–196.
G. Goldstein et al, D. H. Katz, Ed. (CRC Press, 1982), pp. 72–89.
M. K. Waldor et al, manuscript submitted to Science, estimated publication Jan. 1985.

*Primary Examiner*—Johnnie R. Brown
*Assistant Examiner*—John W. Rollins
*Attorney, Agent, or Firm*—Ciotti & Murashige, Irell & Manella

[57] ABSTRACT

Certain autoimmune diseases such as multiple sclerosis, rheumatoid arthritis, and systemic lupus erythematosus may be prevented or attenuated by in vivo treatment with a complement-fixing anti-Leu3 (CD4) antibody that is cytotoxic to Leu3 (CD4) phenotype T cells.

7 Claims, No Drawings

METHOD OF TREATING AUTOIMMUNE DISEASES THAT ARE MEDIATED BY LEU3/CD4 PHENOTYPE T CELLS

REFERENCE TO GOVERNMENT GRANTS

This invention was made with Government support under grants nos. NS-571, NS-18325, GM-17367, HD-01287, and CA-04681 awarded by the National Institutes of Health. The Government has certain rights in this invention.

DESCRIPTION

1. Technical Field

This invention is in the field of immunotherapy. More particularly, it concerns a method of treating Leu3 phenotype T cell mediated autoimmune diseases using anti-Leu3 antibody.

2. Background Art

Autoimmunity (immunity to autoantigens) plays a central role in many immunologic diseases. It is believed to arise from an immunologic imbalance of B cell activity and certain T cell activity, in particular, a disturbance of the balance between suppressor and helper activity of regulatory T cells. Studies of the distribution of T cell subsets in autoimmune disease models or patients indicate that particular T cell subsets are involved in given autoimmune diseases. For instance, human helper T cells of the Leu3 (T4) phenotype (called L3T4 in mice) are involved in the pathogenesis of multiple sclerosis and the corresponding laboratory model, experimental allergic encephalomyelitis (EAE). *Science* (1983) 219: 308–310. Laboratory animals depleted of T cells have exhibited a loss of ability to develop EAE, *J Exp Med* (1962) 116: 177–186 and *Science* (1974) 186: 839–841.

A rat monoclonal antibody that recognizes L3T4 phenotype murine T cells and is highly cytolytic in the presence of complement is described in *Immunological Rev* (1983) 74: 30–56. A counterpart murine monoclonal antibody to Leu3 is described in *J Exp Med* (1981) 153: 193–198. *Monoclonal Antibodies and T Cell Products* (1982) CRC Press, Katz, D. H., Ed., pp 71–89 describes a murine monoclonal antibody, designated OKT4, that recognizes human helper/inducer T cells selectively. This reference states that autoimmune diseases, including rheumatoid arthritis, systemic lupus erythematosus, multiple sclerosis, Sjogren's disease, thyroid disease, and myasthenia gravis, are generally characterized by an increase in the ratio of OKTA4+ T cells to OKT8+ T cells (suppressor/cytotoxic T cells) or a defect in the interrelationship among T cell subsets. In a section titled "Therapeutic Application" this reference says:

"It is interesting to note that those diseases characterized by an altered OKT4/OKT8 ratio may be best treated with an anti-T cell mAb specific for only one T cell subpopulation. Using one of these reagents as a drug may allow the physician the opportunity to selectively delete a subpopulation, either in vivo or perhaps in vitro, which may serve as an effective therapeutic agent if it can be demonstrated that the clinical situation is affected by the imbalance in the T cell subpopulations."

DISCLOSURE OF THE INVENTION

The invention is a method of treating a patient for an autoimmune disease that is mediated by Leu3 phenotype T cells comprising administering a therapeutically effective amount of a complement-fixing, cytotoxic anti-Leu3 antibody to the patient.

MODES FOR CARRYING OUT THE INVENTION

As used herein in connection with human therapy the term "Leu3" is intended to denote a particular membrane antigen that is restricted to human helper T cells. This antigen is described in *J Exp Med* (1981) 153: 193–198. For convenience, the term "Leu3" is sometimes used to denote not only the above described human T cell membrane antigen but homologous T cell membrane antigens that occur in other species.

As used herein the term "monoclonal antibody" means an antibody composition having a homogeneous antibody population, each member of which binds to the same determinant(s).

As used herein the terms "treat" and "therapy", and conjugates thereof are intended to mean prophylaxis or attenuation of existing disease. The invention method may, accordingly, be used to prevent or alleviate autoimmune diseases that are mediated by Leu3+ T cells.

It is believed that the membrane antigens that characterize T cell subsets are highly conserved between mammalian species. Homologs of Leu3 exist, therefore, in other mammalian species. Thus, the invention method may be used to treat autoimmune diseases in mammals, generally, using anti-Leu3 in the case of humans or antibody to a Leu3 homolog for other species. It will, of course, be used primarily to treat humans, and, secondarily, to treat domestic, pet, and sport animals.

As indicated, the autoimmune diseases that may be treated using the invention method are those that are mediated by Leu3 phenotype T cells. Such diseases include multiple sclerosis, rheumatoid arthritis, systemic lupus erythematosus, psoriasis, juvenile onset diabetes, Sjogren's disease, thyroid disease, and myasthenia gravis.

The anti-Leu3 antibody that is used in the treatment may be a monoclonal antibody or purified polyclonal antibody. It is preferably a monoclonal antibody. The mammalian species of the antibody is not critical inasmuch as it appear that anti-Leu3 does not invoke a cross-species antigenic response. In this regard anti-Leu3 may be useful as an immunosuppressant to block immune responses to allogeneic or xenogeneic materials. For instance, it might be co-administered to humans with murine antibodies that are directed to other medical conditions, e.g., cancer, to block the response to the murine antibody. Monoclonal antibodies of current interest will typically be of mouse or rat origin because of the availability of rodent tumor fusion partners for hydribization. Monoclonal antibodies may be made by the somatic cell hybridization procedure first described by Kohler, G. and Milstein, C., *Nature* (1975) 256: 495–497. The tumor cell lines, reagents, and conditions used in this procedure have been reviewed extensively in the literature. (See *Somatic Cell Genetics* (1979) 5: 957–972; *Monoclonal Antibodies* (1980) Plenum Press.) Anti-Leu3-producing lymphocyte fusion partners may be made by immunizing suitable host animals with human peripheral blood lymphocytes or T cell-enriched human peripheral blood lymphocytes.

The anti-Leu3 antibody should be capable of fixing human complement and be highly cytotoxic to the target Leu3+ T cells in the presence of complement. The immunoglobulin class of the antibody is not believed to be critical. It will normally be an IgG of subclass 1 or 2. The antibody will normally have an association constant of at least about $10^7$ L/mol, usually $10^7$ to $10^8$ L/mol.

The antibody may be formulated with conventional pharmaceutically acceptable parenteral vehicles for administration by injection. Such vehicles are inherently nontoxic and nontherapeutic. Examples are water, saline, Ringer's solution, dextrose solution, and Hank's solution. The formulation may contain minor amounts of additives such as substances that maintain isotonicity, physiological pH (e.g., buffers) and stability (preservatives). The antibody is preferably formulated in purified form substantially free of aggregates and other protein at concentrations of about 0.1 to 10 mg/ml. The antibody may be administered parenterally, typically intravenously, as a bolus or in an intermittant or continuous regimen. The dose will depend upon the patient and the patient's medical history. The dose should be sufficient to deplete a substantial portion, usually more than about 90%, of the Leu3+T cell population of the patient. Typical doses for adult humans will range between about 10 and 100 mg. Such amounts are considered "therapeutically effective" as that term is used herein. Doses for children or other animal species may be extrapolated from the adult human dose based on relative body weight.

The following examples further illustrate the invention. These examples are not intended to limit the invention in any manner.

PREVENTION OF EAE WITH ANTI-L3T4

Susceptible SJL/J mice were injected into the tail vein with Bordetella pertussis ($30 \times 10^9$) organisms in 0.5 ml phosphate buffered saline (PBS). The mice were then immunized with 5 mg of mouse spinal cord homogenate (MSCH) in 0.1 ml of a 1:1 eumlsion of complete Freund's adjuvant and PBS containing 4 mg/ml H37Ra mycobacteria in the hind footpads. On day 2 the mice were given a repeat injection of Bordetella pertussis organisms. EAE induced in this way has a characteristic clinical course: the first signs of illness (loss of weight, disheveled coat, and tail weakness) occur 12–15 days after immunization; there is a progression to hind limb paralysis and sometimes to complete paralysis over the next 5–7 days; and by day 21 mice have either died or have recovered and become essentially asymptomatic.

Hybridoma GK1.5 was obtained from Dr. F. W. Fitch. This hybridoma produces a rat antibody of subclass IgG2b that recognizes the L3T4 cell surface antigen of murine helper T cells. L3T4 is the murine homolog of the human T cell surface antigen Leu3. This hybridoma, antibody, and antigen are described in detail in *Immunological Rev.* (1983) 74: 29–56. Hybridoma GK1.5 was grown in serum free HB101 medium. Monoclonal anti-L3T4 was purified to >95% purity from the culture supernatant by precipitation with 50% saturated ammonium sulfate, followed by dialysis to eliminate residual ammonium sulfate and chromatography using QAE-Sephadex A-50 ion exchange gel. The buffer was 50 mM Tris, 150 mM NaCl, pH 8.2. The antibody was diluted to 0.2 mg/ml in PBS for administration to the immunized mice.

Immunized mice were injected with 100 μg of the antibody according to various injection regimens.

A control group was injected only with PBS. The mice were examined at least through day 32 and were scored as sick if they exhibited any signs of illness. Mice were examined histologically for lesions at the end of the test. Six standard sections of brain and spinal cord were examined for each mouse according to the technique described in *PNAS* (USA) (1981) 78: 7111 and *J Exp Med* (1983) 158: 1362. Slides were coded and read by an observer blind with regard to the treatment protocol. Results of these tests are reported in Table 1 below.

TABLE 1

| Treatment | | Clinical disease | | | Histologic disease |
|---|---|---|---|---|---|
| anti-body | injection days | Cumulative incidence (sick/total) | signi-ficance | Mean onset (day) | perivasc-ular cuffs |
| L3T4 | 9,10,11,12 13,14,16,18 20, 22 | 0/10 | p < 0.001 | — | 1/6* |
| L3T4 | 9,10,11,12 | 8/18 | p < 0.005 | 19 | 1/8 |
| L3T4 | −2,−1,1 | 4/15 | p < 0.001 | 27 | 0/9 |
| none (PBS) | −2,−1,1 | 26/30 | — | 14 | 13/13 |

*# of mice with lesions/# of mice examined

These tests show that injection of anti-L3T4 antibody prevents the clinical and histologic manifestations of EAE when the antibody was administered after T cells capable of transferring EAE have been generated. Nine days after immunization with MSCH mice have already developed a T cell population that can transfer EAE to naive recipients. Such MSCH immunized mice failed to develop EAE when injected repeatedly with anti-L3T4 beginning on day 9. When anti-L3T4 was injected on the two days preceding and the day following immunization for the induction of EAE, no mice exhibited disease two weeks later—a time when nearly 90% of PBS injected controls were paralyzed.

REVERSAL OF EAE WITH ANTI-L3T4

SJL/J mice were immunized as above. Antibody treatment was initiated when the mice exhibit mild EAE symptoms (typically on days 12–14). At that time the mice were injected with 300 μg of anti-L3T4 intraperitoneally. The mice received 100 μg injections of anti-L3T4 on each of the two days following treatment initiation.

The clinical status of the mice was graded 72 hr after treatment was initiated according to the following scale: nil, no neurologic symptoms or residual tail weakness with weight gain; mild, a flaccid tail and paraparesis with weight loss and poor coat texture; or severe, quadriplegia with hind limb scissoring. The clinical conditions were graded by an observer who was blind with regard to the treatment protocol.

The number of mice dead at day 7 was recorded.

The results of these tests are reported in Table 2 below.

TABLE 2

| | Number of mice exhibiting clinical symptoms | | | | |
|---|---|---|---|---|---|
| | Before treatment was initiated | 72 hr after treatment was initiated | | | |
| Treatment | (mild) | (nil) | (mild) | (severe) | Deaths |
| anti-L3T4 | 16 | 14 | 1 | 1 | 1 |
| none (PBS) | 16 | 1 | 2 | 13 | 6 |

As shown in Table 2 treatment with anti-L3T4 was effective even when mice were injected with the antibody after the first signs of EAE were apparent. Unlike the control mice, the anti-L3T4-treated mice did not progress to hind limb paralysis, quadriplegia or death, and by 72 hr after anti-L3T4 treatment began, 90% of the treated mice showed clinical improvement with no residual neurologic deficit. Treatment of quadriplegic or moribund mice with anti-L3T4 did not ameliorate paralysis or prevent death.

EFFECT OF ANTI-L3T4 TREATMENT ON T CELL POPULATION

Multiparameter fluorescent activated cell sorter (FACS) analysis was used to investigate the changes in the frequencies of T cells belonging to different T cell subsets following treatment with anti-L3T4 antibody (100 μg on each of the two days prior to FACS analysis). To estimate the frequency of L3T4+ cells in animals treated with anti-L3T4 antibody, the Ly1 and Lyt2 surface markers were used. With dual immunofluorescence analyses these surface markers provide an accurate estimate of L3T4+ T cell frequency, since L3T4+ cells are Ly1+Lyt2− and L3T4− cells are Ly1+Lyt2+.

Preparation of cells, staining procedures, and data collection were as described in *J Exp Med* (1983) 157: 202. Spleen and pooled popliteal, inguinal, axillary and brachial lymph node cells were stained with fluorescein conjugated anti-Lyt2 together with biotin anti-Ly1 (*Eur J Immunol* (1980) 10: 1) followed by Texas red avidin and analyzed on a dual laser FACS equipped with logarithmic amplifiers. Contour plots of the amounts of the respective antigens as revealed by fluorescence intensity were made. These contour plots are representations of three dimensional surfaces in which the levels of green and red fluorescence per cell define locations on a two dimensional surface, and the frequency of cells with that value of fluorescence defines the elevation at that location. After this surface is smoothed, contour lines are drawn to divide the sample into equal fractions. Integration boundaries shown in the plots are used to determine the frequency of Ly1+Lyt2− and Ly1+Lyt2+ cells. The number of cells of a given phenotype was estimated by multiplying the cell frequency by the cell count for the organ in question. The results of these tests are reported in Table 3 below.

TABLE 3

| T cell sub-set | surface phenotype measurement | spleen | | lymph nodes | |
|---|---|---|---|---|---|
| | | un-treated (x10$^6$) | anti-L3T4 treated (x10$^6$) | un-treated (x10$^6$) | anti-L3T4 treated (x10$^6$) |
| L3T4+ | Ly1+Lyt2− | 28 | 16 | 25 | 3.1 |
| Lyt2+ | Ly1+Lyt2+ | 8.3 | 8.8 | 14 | 16 |

Table 3 shows that anti-L3T4 antibody treatment selectively depletes L3T4+ T cells. Two injections of anti-L3T4 antibody at 24 hr intervals are sufficient to deplete about half of the splenic L3T4+ cells and nearly all of this T cell subset from lymph nodes. Similar depletions of the L3T4+ subset occur in mice that have already been immunized for the induction of EAE and treated with anti-L3T4 on days 9–12 (data not reported). The T cell depletion was specific for the L3T4+ subset since the numbers of Ly1+Lyt2+ (L3T4− T cells) were not altered by the anti-L3T4 antibody treatment. Interestingly, thymocytes were not appreciably altered by the anti-L3T4 antibody treatment and the percentage of L3T4+ thymocytes was not significantly changed in treated mice (data not reported).

The mechanism of the therapeutic action of anti-L3T4 antibody administration is still obscure. The observed depletion in the numbers of peripheral L3T4+ inducer, helper or effector T cells may alone account for the attenuation of disease. Alternatively, the ability of the antibody to bind L3T4 and block the functional activities of this molecule could also play a role. In addition the depletion and/or blockage of L3T4+ cells may result in a shift in the balance between regulatory helper and suppressor T cells to an alternate stable state in which suppression becomes the dominant response to the encephalitogenic components of MSCH. Regardless of the mechanism of action of anti-L3T4 antibody treatment, the above results show that in vivo administration of anti-L3T4 antibody has a dramatic effect on the course of EAE.

Modifications of the above described modes for carrying out the invention that are obvious to persons of skill in medicine, immunology, hybridoma technology, pharmacology and/or related fields are intended to be within the scope of the following claims.

We claim:

1. A method of treating a patient for an autoimmune disease that is mediated by Leu3(CD4) phenotype T cells comprising parenterally administering a therapeutically effective amount of an anti-Leu3(CD4) antibody that binds to said T cells to the patient.

2. The method of claim 1 wherein the patient is a human.

3. The method of claim 2 wherein the disease is multiple sclerosis, rheumatoid arthritis, systemic lupus erythematosus, psoriasis, juvenile onset diabetes, Sjogren's disease, thyroid disease, or myasthenia gravis.

4. The method of claim 1 wherein the disease is multiple sclerosis.

5. The method of claim 1 wherein said amount is in the range of about 10 and about 100 mg.

6. The method of claim 1 wherein said antibody is a monoclonal antibody of class IgG1 or IgG2.

7. The method of claim 6 wherein the association constant of the antibody is at least about $10^7$ L/mol.

* * * * *

UNITED STATES PATENT AND TRADEMARK OFFICE

Certificate

Patent No. 4,695,459　　　　　　　　　　　　　　　　　　　　Patented: Sept. 22, 1987

On motion pursuant to 37 CFR 1.634 in Interference No. 102,186, it has been found that the above-identified patent, through error and without any deceptive intention, incorrectly sets forth the inventorship. Accordingly, pursuant to 35 U.S.C. 256 it is certified that the correct inventorship of this patent is: Lawerence Steinman, Matthew K. Waldor, Subramanian Sriram, Leonard A. Herzenberg, Leonore A. Herzenberg and Steven W. Brostoff.

Signed and Sealed this 24th Day of April 1990.

MICHAEL SOFOCLEOUS

*Examiner-in-Chief*
　　　　　　　　　　　　　　　　　　　　　　　　　　　　　　　*Board of Patent Appeals*
　　　　　　　　　　　　　　　　　　　　　　　　　　　　　　　　　*and Interferences*